(12) United States Patent
Winslow

(10) Patent No.: US 7,585,327 B2
(45) Date of Patent: Sep. 8, 2009

(54) EXTENDED ARTICULAR SURFACE RESURFACING HEAD

(75) Inventor: Nathan A Winslow, Warsaw, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 164 days.

(21) Appl. No.: 10/669,971

(22) Filed: Sep. 24, 2003

(65) Prior Publication Data

US 2005/0065612 A1    Mar. 24, 2005

(51) Int. Cl.
*A61F 2/40* (2006.01)
(52) U.S. Cl. ............... 623/19.14; 623/19.11; 623/23.42
(58) Field of Classification Search ............... 623/19.11, 623/19.12, 19.13, 19.14, 23.42, 23.12, 23.13, 623/23.14, 21.15, 21.19, 23.4
See application file for complete search history.

(56) References Cited

U.S. PATENT DOCUMENTS

| | | | |
|---|---|---|---|
| 3,979,778 A | | 9/1976 | Stroot et al. |
| 4,042,980 A | | 8/1977 | Swanson et al. |
| 4,261,062 A | | 4/1981 | Amstutz et al. |
| 4,328,593 A | * | 5/1982 | Sutter et al. ............... 623/23.42 |
| 4,470,158 A | * | 9/1984 | Pappas et al. ............ 623/20.21 |
| 4,550,450 A | | 11/1985 | Kinnett |
| 4,919,670 A | | 4/1990 | Dale et al. |
| 5,314,479 A | | 5/1994 | Rockwood, Jr. et al. |
| 5,358,526 A | | 10/1994 | Tornier |
| 5,549,682 A | | 8/1996 | Roy |
| 5,910,171 A | | 6/1999 | Kummer et al. |
| 6,045,582 A | | 4/2000 | Prybyla |
| 6,120,542 A | | 9/2000 | Camino et al. |
| 6,129,764 A | | 10/2000 | Servidio |
| 6,197,062 B1 | | 3/2001 | Fenlin |
| 6,197,063 B1 | | 3/2001 | Dews |
| 6,589,282 B2 | | 7/2003 | Pearl |
| 6,620,197 B2 | | 9/2003 | Maroney et al. |
| 6,673,114 B2 | | 1/2004 | Hartdegen et al. |
| 6,783,549 B1 | | 8/2004 | Stone et al. |
| 2001/0047210 A1 | | 11/2001 | Wolf |
| 2002/0022889 A1 | * | 2/2002 | Chibrac et al. ........... 623/18.11 |
| 2002/0099381 A1 | | 7/2002 | Maroney |
| 2002/0099445 A1 | | 7/2002 | Maroney et al. |
| 2003/0028253 A1 | | 2/2003 | Stone et al. |

(Continued)

FOREIGN PATENT DOCUMENTS

DE    42 20 217    12/1993

(Continued)

OTHER PUBLICATIONS

Copeland Humeral Resurfacing Head (Biomet Orthopedics, Inc.: 2000 brochure).*

(Continued)

*Primary Examiner*—David H Willse
*Assistant Examiner*—Javier G Blanco
(74) *Attorney, Agent, or Firm*—Harness, Dickey

(57) ABSTRACT

A resurfacing implant comprising a head and an extended articulating surface protruding from a portion of the head operable to articulate with at least one of a bone and a ligament. The head has an exterior articulating surface, an interior surface opposite the exterior articulating surface, and an anchoring device extending from the interior surface.

14 Claims, 3 Drawing Sheets

U.S. PATENT DOCUMENTS

| | | |
|---|---|---|
| 2003/0144738 A1 | 7/2003 | Rogalski |
| 2004/0002765 A1 | 1/2004 | Maroney et al. |
| 2004/0034431 A1 | 2/2004 | Maroney et al. |
| 2004/0193277 A1* | 9/2004 | Long et al. ............... 623/19.14 |
| 2004/0193278 A1 | 9/2004 | Maroney et al. |
| 2005/0021038 A1 | 1/2005 | Maroney |
| 2006/0036328 A1 | 2/2006 | Parrott et al. |
| 2007/0198094 A1 | 8/2007 | Berelsman et al. |

FOREIGN PATENT DOCUMENTS

| | | |
|---|---|---|
| EP | 0 617 934 | 10/1994 |
| EP | 0 845 250 A2 | 6/1998 |
| EP | 1 064 890 A1 | 1/2001 |
| EP | 1 464 305 | 10/2004 |
| FR | 2 578 739 | 9/1986 |
| FR | 2880793 | 7/2006 |

OTHER PUBLICATIONS

"Global Advantage CTA Humeral Head," Depuy Orthopaedics, copyright 2000 (2 pages).

Two engineering drawings illustrating a humeral head replacement device. Jul. 22, 1997.

\* cited by examiner ized at reference numeral 10. The implant 10 is typically
EXTENDED ARTICULAR SURFACE RESURFACING HEAD

FIELD OF THE INVENTION

The present invention relates to prosthetic implants. In particular, the present invention relates to a humeral resurfacing implant.

BACKGROUND OF THE INVENTION

The humerus is the longest and largest bone of the human upper extremity. It is divisible into a body and two extremities. The upper extremity comprises a head that is joined to the body by a constricted portion generally called the neck. The head is nearly hemispherical in form and articulates with the glenoid cavity of the scapula or shoulder blade. The humerus is secured to the scapula by the rotator cuff muscles and tendons.

It is not uncommon for the exterior surface of the humeral head to be damaged or defective. Conventionally, a variety of humeral head resurfacing implants exist for repairing humeral head surfaces. While conventional humeral head resurfacing implants are suitable for their intended uses, such implants are subject to improvement.

Conventional humeral head resurfacing implants fail to accommodate patients having inadequate rotator cuff muscles. Specifically, conventional implants do not permit articulation between the implant and the concave undersurface of the coracoacromial arch of the scapula, the coracoacromial arch being a structural component of the shoulder comprising the coracoacromial ligament, coracoid process, and acromion. Thus, there is a need for a humeral head resurfacing implant that permits articulation with the coracoacromial arch in patients having inadequate rotator cuff muscles.

SUMMARY OF THE INVENTION

In one embodiment, the present invention provides for a resurfacing implant comprising a head and an extended articulating surface protruding from a portion of the head operable to articulate with at least one of a bone and a ligament. The head has an exterior articulating surface, an interior surface opposite the exterior articulating surface, and an anchoring device extending from the interior surface.

In another embodiment, the present invention provides for a humeral head resurfacing implant comprising a humeral head having an articulating surface, an engagement stem extending from the head, and an extended surface protruding from the head operable to articulate with at least one element of a coracoacromial arch.

In yet another embodiment, the present invention provides for a method for resurfacing a humeral head of an implant site. The method comprises preparing the humeral head and implanting an implant at the humeral head. The implant has an exterior articulating surface, an interior surface opposite the exterior surface, a stem extending from the interior surface, and an extended articulating surface operable to articulate with at least one element of a coracoacromial arch.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
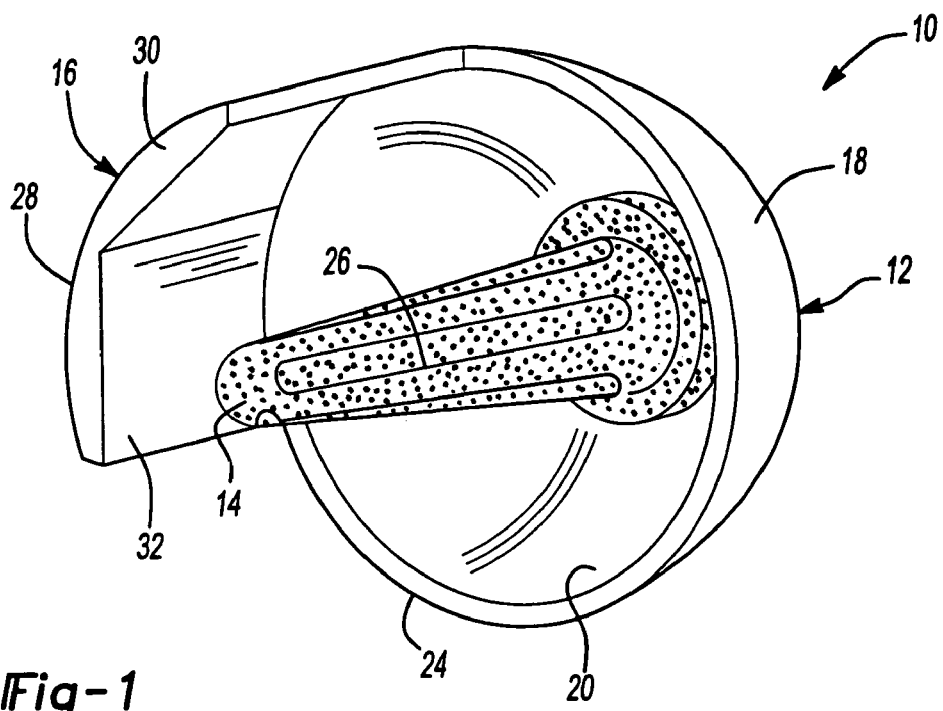
FIG. 1 is a perspective view of an implant according to the present invention.
Figure 2:
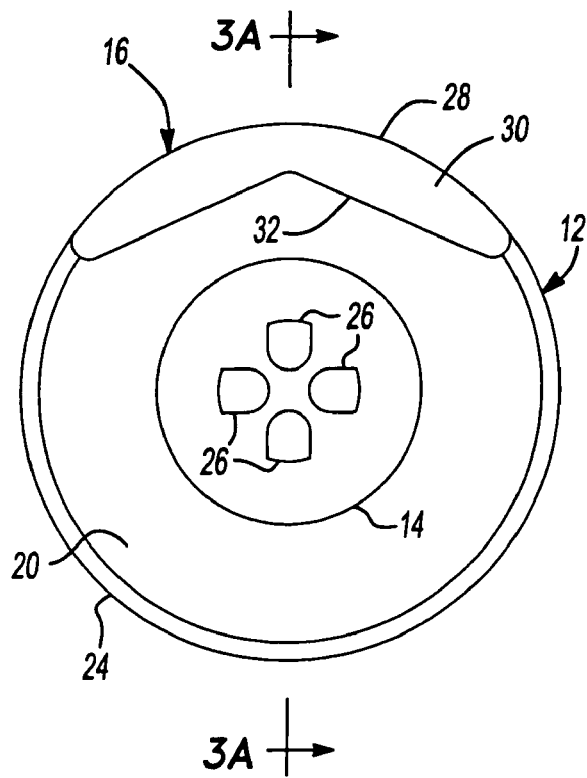
FIG. 2 is bottom view of the implant of FIG. 1.

With initial reference to FIGS. 1 through 3, a resurfacing implant according to the present invention is illustrated and identified at reference numeral 10. The implant 10 is typically divided into, as illustrated in FIG. 3, a lateral region A and a medial region B, which is in relation to the implant position in the patient. The implant 10 generally includes a resurfacing head 12, an anchoring device or stem 14, and an extended surface 16. The extended surface 16 may be located in the lateral region A, as illustrated, or at any other position about a periphery of the head 12. The head 12 includes an exterior surface 18 and an interior surface 20 opposite the exterior surface 18. The exterior surface 18 is generally convex, or dome-shaped, and smooth. The interior surface 20 is generally concave.

The interior surface 20 is also generally dome-shaped and substantially mirrors the exterior surface 18. The interior surface 20 is generally concave. The interior surface 20 may be smooth or may include features, such as pores or coatings, that facilitate bonding of the interior surface 20 to a resurfaced implant site. The interior surface 20 may be bonded to the implant site with or without bone cement. The interior surface 20 optionally terminates at an annular rim 24.

The stem 14 extends from the interior surface 20. The stem 14 may optionally be tapered such that the diameter of the stem 14 is at its greatest at the interior surface 20. To facilitate cooperation between the stem 14 and the implant site, the stem 14 may optionally include one or more details, such as flutes 26. In addition to or in place of flutes 26, the stem 14 may include surface features, such as pores or coatings, to enhance the creation of a bond between the stem 14 and the implant site.

Figure 3A:
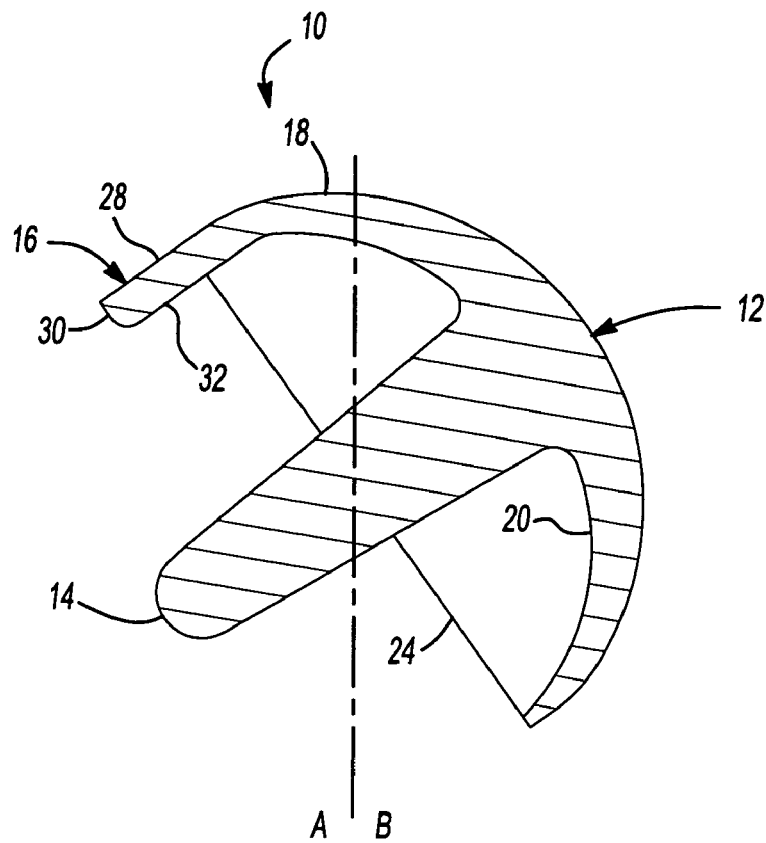
FIG. 3A is a cross-sectional view taken along line 3-3 of FIG. 2.

In some applications, the extended surface 16 is located in the lateral region A to engage a surface or bone, such as at least one portion of the coracoacromial arch. However, the extended surface 16 may be located at any other position about the rim 24 to engage a variety of different bones and/or ligaments. The extended surface 16 is generally comprised of an outer surface 28, a base surface 30, and an inner surface 32. The outer surface 28 is typically a continuation of the exterior surface 18. The outer surface 28 may be of any suitable shape or configuration, however, in many instances, the outer surface 28 is curved or rounded to follow the general shape of the exterior surface 18. The outer surface 28 extends about a portion, but less than an entirety of the annular rim 24. The extended surface 16 generally extends beyond an equator of the hemispherical head 12, which is generally defined by the rim 24. As seen in FIG. 3A, the extended surface 16 extends from the head 12 in a planar and/or cylindrical manner.

The base surface 30 generally extends from the outer surface 28 toward the stem 14 at approximately a right angle to the outer surface 28. The base surface 30 may be generally planar or may include various surface features to enhance interaction between the base surface 30 and the implantation site. The base surface 30 is typically shaped to accommodate the curvature of the annular rim 24. The length of the base surface 30 determines, in part, the width of the extended surface 16.

The inner surface 32 extends from the base surface 30 toward the interior surface 20. The inner surface 32 extends from the base surface 30 at an approximate right angle to the base surface 30. The inner surface 32 may be of any suitable shape but is typically shaped to generally accommodate the curvature of the annular rim 24. In some applications, the inner surface 32 may be wedged shaped, typically in the shape of a "V", to generally facilitate interaction between the implant 10 and the implantation site by providing a surface that matches the shape of a prepared bone that is to receive the implant 10. The shape of the inner surface 32, such as the wedge shape, may be used to act as a further aide to maintain the implant 10 in its desired position and prevent rotation of the implant 10 at the implantation site.

Figure 3B:
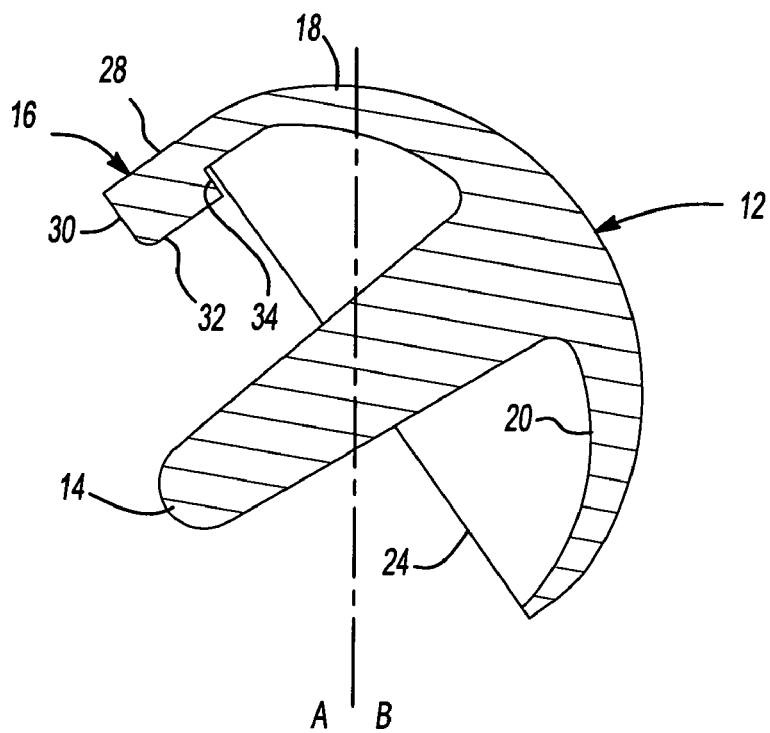
FIG. 3B is a cross-sectional side view of the implant of the present invention according to an additional embodiment.

If the extended surface 16 is of a relatively small width, the inner surface 32 may be an extension of the interior surface 20 (FIG. 3A). As illustrated in FIG. 3B, if the extended surface 16 is of a relatively large width, the inner surface 32 is not a continuation of the interior surface 20, but is connected to the interior surface 20 by an upper surface 34. The upper surface 34 runs generally parallel to the base surface 30 and may be, for example, planar or curved. The upper surface 34 forms a step on the extended surface 16.

The implant 10 may be made of any suitable biocompatible material, but is typically made from a metal such as cobalt chrome or titanium. The interior surface 20 may be coated with a suitable material, such as titanium plasma spray or hydroxyapatite, to enhance the adhesion of the interior surface 20 to the implantation site or to enhance the effectiveness of any material, such as bone cement, that may be used to affix the interior surface 20 to the implantation site. The stem 14 may optionally be provided with a blasted finish, with or without hydroxyapatite, or a micro-bond finish, with or without hydroxyapatite. As a further option, bone cement may be used as an aide to retain the implant 10 in position.

The implant 10 may be of various different sizes and dimensions depending on the sizes and dimensions of the implant site. For example, to accommodate patients having large humeral heads, the implant 10 may be of a greater overall size than that required to accommodate patients having smaller humeral heads. Further, the shape of the exterior surface 18 may be customized to insure proper articulation at the implant site. Implants 10 of various different shapes and sizes may be packaged together and sold in a single kit.

Figure 4:
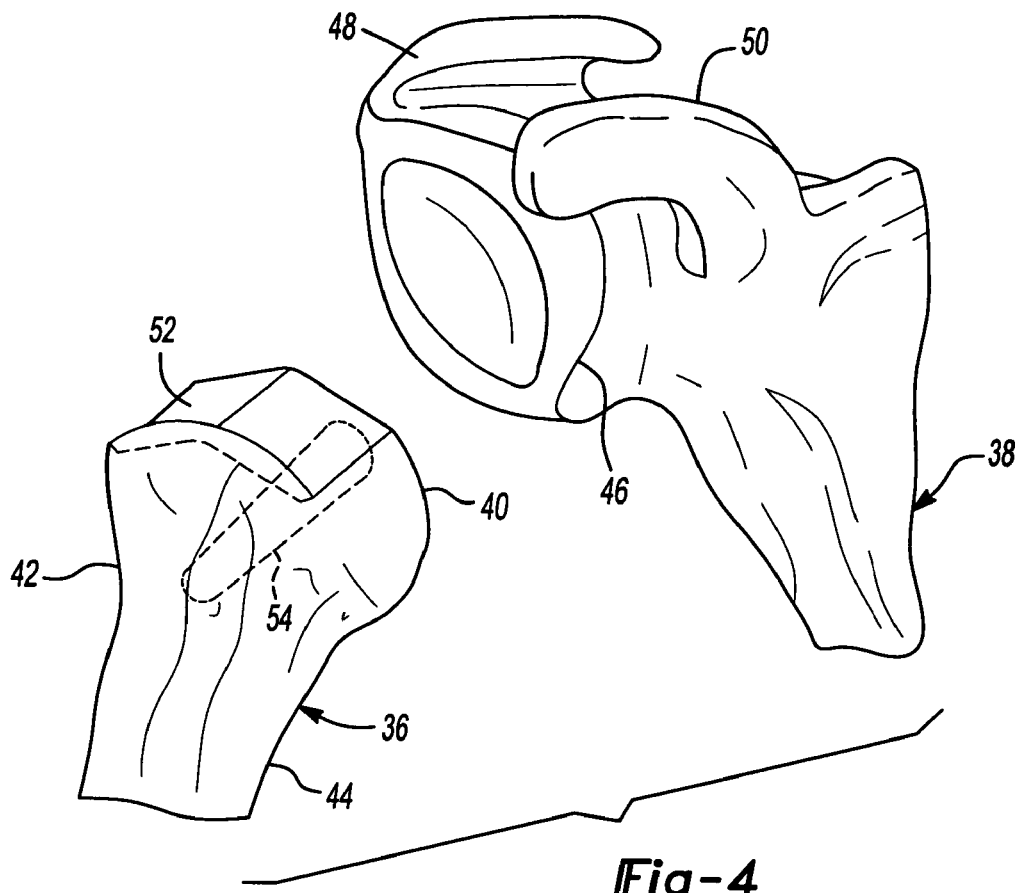
FIG. 4 is a perspective view of a typical implantation site prepared to receive the implant of FIG. 1.
Figure 5:
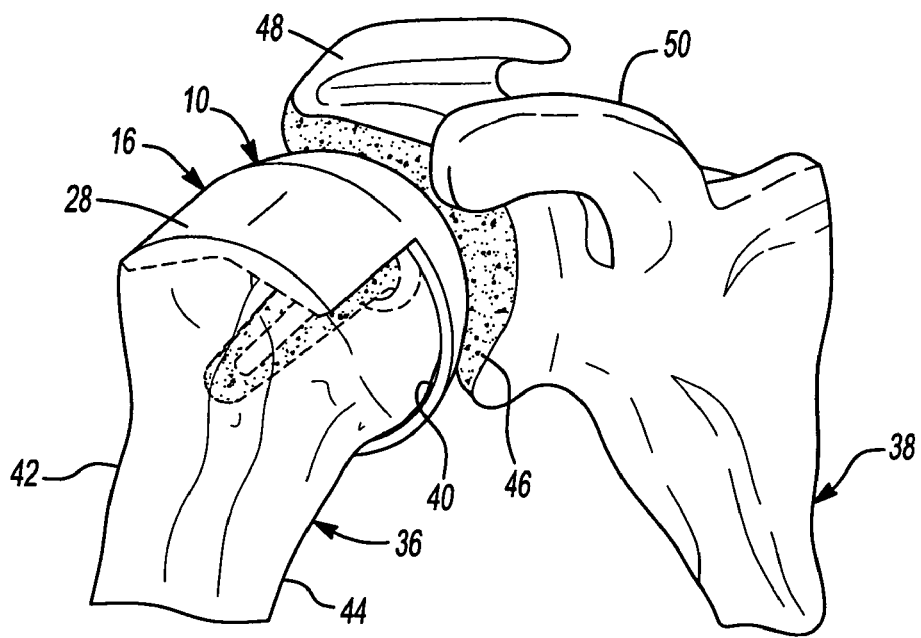
FIG. 5 is a perspective view of the implant of FIG. 1 implanted at the implantation site of FIG. 4.

With reference to FIGS. 4 and 5, the implantation and operation of the implant 10 will be described in detail. While the implant 10 is generally described as a humeral head resurfacing implant, it must be noted that the implant 10 may be used in a variety of different applications. The implantation site generally includes a humerus 36 and a shoulder blade or scapula 38. The humerus 36 is generally comprised of a head 40, a neck 42, and a stem 44. The scapula 38 is generally comprised of a glenoid cavity 46 that receives the head 40, a coracoacromial arch 48, and a coracoid process 50.

To receive the implant 10, a portion of the exterior surface of the humeral head 40 is resurfaced and/or removed to accommodate the resurfacing head 12 of the implant 10 such that, when implanted, the implant head 12 does not generally increase the overall dimensions of the humeral head 40. The head 12 is further resected at 52 to accommodate the extended surface 16. This resection at 52 may be performed with or without the use of a resection jig. To minimize bone loss, the resection at 52 often takes the shape of a "V", however, the resection 52 may be of various other shapes or configurations. The "V" shape may also prevent rotation of the head 12, even though the interaction between the stem 14 and the implant site is more than adequate to secure the head 12 into position.

To receive the stem 14, which is generally referred to as a short stem 14, a peg hole 54 is formed within the head 40 using conventional instruments and techniques. The hole 54 is formed with dimensions substantially similar to the dimensions of the stem 14 and is positioned such that when the stem 14 is seated within the hole 54, the exterior surface 18 closely approximates the outer surface of the humeral head 40. The hole 54 extends generally only through a portion of the humeral head 40 and does not necessarily extend to the stem 44 or within the intramedullary canal of the humerus. To ensure proper placement of the implant 10, a trial implant (not shown) may be positioned at the implantation site before the implant 10 is implanted.

The trial implant is substantially similar to the implant 10. A stem of the trial implant is placed within the hole 54 and the shoulder joint is reduced. If necessary, the head 40 is reamed to better approximate the size and shape of the interior surface 20. After the proper position of the trial implant is noted, the trial is removed and the stem 14 of the implant 10 is seated within the hole 54. The implant 10 is then positioned such that it is in substantially the same position as the trial implant. The particular size of the implant 10 is chosen according to the size and dimensions of the patient's humeral head 40 and scapula 38. It must be noted that typically the stem 14 only extends through a portion of the head 40 and does not enter, or replace, the natural stem 44 of the humerus 36.

As illustrated in FIG. 5, the implant 10 is orientated at the humeral head 40 such that the extended surface 16 is positioned at or near the coracoacromial arch 48. The extended surface 16 may either abut, or closely abut, the coracoacromial arch 48. When the patient's rotator cuff muscles are inadequate, the extended surface 16 typically contacts the coracoacromial arch to provide metal on bone articulation with the coracoacromial arch 48. However, the extended surface 16 may be rotated to any other position to engage other bones, ligaments, or surfaces other than, or in addition to, the coracoacromial arch 48.

While interaction between the stem 14 and the hole 54 is typically suitable to secure the implant 10 within the hole 54, the stem 14 may optionally be secured within the hole 54 using a suitable adhesive, such as bone cement 56. The optional bone cement 56 may be inserted within the hole 54, typically before the implant 10 is placed within the hole 54. The flutes 26 of the stem 14 assist in forming a cement mantle between the stem 14 and the hole 54 to receive the bone cement 56. The optional tapered configuration and blasted finish of stem 14 further enhances the bond between the implant 10 and the head 40 by providing a mechanical interface. To still further secure the implant 10 to the head 40, a suitable adhesive, such as bone cement, may be placed between the interior surface 20 and the head 40 and various coatings may be applied to the interior surface 20, such as titanium plasma, to create a bond between the interior surface 20 and the head 40.

With the implant 10 in place upon the humeral head 40, patients with inadequate rotator cuff muscles are provided with a device that permits articulation between the humerus 36 and the coracoacromial arch 48. This articulation between the humerus 36 and the coracoacromial arch 48 enhances range of motion in the patient's shoulder and reduces patient discomfort.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A monolithic humeral head resurfacing implant comprising:
    a head having:
        a hemispherical exterior articulating surface defining a terminating rim;
        a concave interior surface opposite said hemispherical exterior articulating surface;
        an integral straight anchoring stem having a textured outer surface configured to be directly coupled to bone, said anchoring stem extending from said interior surface and being integral with the interior surface; and
        an extended articulating surface defining a flange axially protruding from only a portion of the terminating rim of said hemispherical exterior articulating surface, said extended articulating surface operable to articulate with at least one of a bone and a ligament, said extended articulating surface having a pair of interior intersecting flat planar surfaces, said interior intersecting flat planar bone bearing surfaces being generally parallel to the integral straight anchoring stem, wherein said extended articulating surface is located in a lateral region of said head when implanted in a patient, and wherein said pair of interior intersecting flat planar surfaces define a planar "V" shaped inner surface defined on the extended articulating surface.

2. The implant of claim 1, wherein said extended articulating surface articulates with at least one element of a coracoacromial arch.

3. The implant of claim 1, wherein said implant is comprised of at least one of cobalt chrome, titanium, and a biocompatible material.

4. The implant of claim 1, wherein said stem includes flutes.

5. The implant of claim 1, wherein said stem includes a first end proximate to said head and a second end distal to said head, said second end having a diameter that is smaller than said first end.

6. The implant of claim 1, wherein said stem includes a blasted finish.

7. The implant of claim 1, wherein said extended articulating surface includes an outer surface that is substantially flush with said exterior articulating surface.

8. A monolithic humeral head resurfacing implant comprising:
    a humeral head having a hemispherical exterior articulating surface and a concave interior coupling surface, said hemispherical articulating surface terminating at a rim at a hemispherical equator;
    an integral engagement stem configured to be directly coupled to bone, said stem extending from said head, said stem being integral with the concave coupling surface; and
    an extended articulating surface defining a flange axially protruding from only a portion of the terminating rim of said hemispherical equator of said hemispherical articulating surface and operable to articulate with at least one element of a coracoacromial arch, said extended articulating surface having a pair of interior intersecting flat planar surfaces, said interior intersecting flat planar surfaces being generally parallel to the integral engagement stem, wherein said extended articulating surface is located in a lateral region of said head when implanted in a patient, and wherein said pair of interior intersecting flat planar surfaces define a planar "V" shaped inner surface defined on the extended articulating surface.

9. The implant of claim 8, wherein said engagement stem further comprises flutes.

10. The implant of claim 8, wherein said engagement stem is tapered.

11. The implant of claim 8, wherein said extended surface is positioned at a lateral region of the implant when implanted in a patient.

12. A method for resurfacing a humeral head of an implant site, the method comprising:
    resurfacing the humeral head so as to remove a portion of the humeral head leaving a resurfaced surface;
    boring a hole into the humeral head;
    resecting a portion of the humeral head so as to form a resected head having a pair of intersecting flat planar surfaces, said surfaces being generally parallel to the hole;
    positioning a resurfacing humeral head implant adjacent said flat planar surfaces, after resecting said portion of the humeral head to form said pair of intersecting flat planar surfaces, said resurfacing head implant having a hemispherical exterior articulating surface which terminates at a rim at a hemispherical equator of the resurfacing humeral head implant, a concave interior surface, an integral engagement stem, and an extended articulating surface defining a flange axially protruding from only a portion of the terminating rim of said hemispherical equator of said hemispherical exterior articulating surface, said extended articulating surface having a pair of interior intersecting flat planar surfaces, said interior intersecting flat planar surfaces of the flange being generally parallel to the integral engagement stem, wherein said extended articulating surface is located in a lateral region of said humeral head implant when implanted in a patient, and wherein said pair of interior intersecting flat planar surfaces define a planar "V" shaped inner surface defined on the extended articulating surface;
    aligning the pair of interior intersecting flat planar surfaces of the flange with the pair of intersecting flat planar surfaces formed on the bone; and
    positioning the extended articulating surface of the resurfacing humeral head implant in a lateral region of the resected humeral head so as to articulate with at least one of a bone and a ligament and interface with the pair of intersecting flat planar surfaces formed on the bone.

13. The method of claim 12, wherein said resurfacing step comprises resecting a portion of the humeral head to receive the extended articulating surface.

14. The method of claim 12, wherein resurfacing the humeral head comprises forming a hole only within the humeral head, the hole operable to receive a short stem of the implant.

* * * * *